(12) United States Patent
Friedlander et al.

(10) Patent No.: US 7,516,019 B2
(45) Date of Patent: Apr. 7, 2009

(54) METHOD FOR ONLINE MEASUREMENT OF ULTRAFINE AGGREGATE SURFACE AREA AND VOLUME DISTRIBUTIONS

(75) Inventors: Sheldon K. Friedlander, Los Angeles, CA (US); Anshuman A. Lall, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 313 days.

(21) Appl. No.: 11/495,154

(22) Filed: Jul. 28, 2006

(65) Prior Publication Data

US 2007/0043520 A1    Feb. 22, 2007

Related U.S. Application Data

(60) Provisional application No. 60/703,728, filed on Jul. 29, 2005.

(51) Int. Cl.
*G01N 31/00* (2006.01)
(52) U.S. Cl. .................. 702/29; 422/151; 428/403

(58) Field of Classification Search .................. 702/26, 702/29; 422/151; 427/212; 428/403
See application file for complete search history.

(56) References Cited

U.S. PATENT DOCUMENTS

2003/0235689 A1* 12/2003 Rafaniello et al. .......... 428/403
2006/0159596 A1*  7/2006 De La Veaux et al. ....... 422/151

* cited by examiner

*Primary Examiner*—John H Le
(74) *Attorney, Agent, or Firm*—Ladas & Parry, LLP

(57) ABSTRACT

Method for the online measurement of the number, surface area and volume distribution of nanoparticle aerosol aggregates relates the number and size of primary particles that compose the aggregates and the aggregate mobility diameter. The number distribution of nanoparticle aggregates is obtained by calculations based on the drag on the aggregates and the aggregate charging efficiency. The aggregate surface area and volume are obtained by summing over the surface areas and volume of the primary particles that compose the aggregate. The aggregate surface area and volume distribution is then obtained by multiplying the aggregate surface area, volume and the aggregate number distribution.

20 Claims, 13 Drawing Sheets

US 7,516,019 B2

METHOD FOR ONLINE MEASUREMENT OF ULTRAFINE AGGREGATE SURFACE AREA AND VOLUME DISTRIBUTIONS

RELATED APPLICATIONS

This patent application claims the priority of U.S. Ser. No. 60/703,728 filed on Jul. 29, 2005, the entire contents of which are incorporated herein by reference thereto.

This invention was made with Government support of Grant No. ATM 0124590, awarded by the National Science Foundation. The Government has certain rights in this invention.

TECHNICAL FIELD

This disclosure relates to methods and systems for online measurement of the number, surface area, volume, and distribution thereof of aggregates in a flowing gas stream.

BACKGROUND

Differential mobility analyzers are often used to measure the number, size and distribution of aerosol particles (Pui, D. Y. H., and Swift, D. L., Direct-Reading Instruments for Airborne Particles In Air Sampling Instruments for Evaluation of Atmospheric Contaminants (Edited by Hering S. V., and Cohen, B. S., pp. 337-368, ACGIH, Inc., Ohio (1995)). However, because these instruments are calibrated for spherical particles, the calibrations are not directly applicable for non-spherical particles and can not be used to obtain surface area and volume distributions of non-spherical particles and nanoparticle chain aggregates (NCA).

Aggregates appear in the emissions from diesel engines (Park, K., Kittelson, D. B., Zachariah M. R. and McMurry, P. H. "Measurement of Inherent Material Density of Nanoparticle Agglomerates", J. Nanoparticle Res. 6, 267 (2004)); (Martins, J. V., Artaxo, P., Liousse, C., Reid, I. S., Hobbs, P. V., and Kaufmann, Y. J., "Effects of Black Carbon Content, Particle Size, and Mixing on Light Absorption by Aerosol from Biomass Burning in Brazil", J Geophys. Res. 103, 32041, (1998)), and are generated in the commercial production of fine particles (Kodas, T. T., and Hampden-Smith, M., "Aerosol Processing of Materials," Wiley-VCH, New York., 1999). They also appear in the manufacture of carbon black, silica and titania (Pratsinis, S. E., "Flame Aerosol Synthesis of Ceramic Powders", Prog. Energy Combust. Sci. 24, 197, (1998)) as well as byproducts of many manufacturing procedures. Thus NCAs constitute an important class of materials which can not be properly or accurately monitored by use of the standard calibration for spheres.

There is thus a need for a more reliable, reproducible on-line method capable of measuring aggregate surface area and volume distributions as a function of a properly defined aggregate size. The embodiments of the present disclosure answer these and other needs.

SUMMARY

In a first embodiment disclosed herein, a method of estimating the number of nanoparticle aerosol aggregates having a primary particle size a in a gas using a differential mobility analyzer for measuring spherical particles comprises passing a volume of a gas containing entrained nanoparticle aerosol aggregates through a differential mobility analyzer for measuring spherical particles; obtaining the primary particle size a of the aggregates; obtaining the mobility diameter $d_m$ of the aggregates; counting the total number of aggregates that pass through the analyzer $n_{sph}$; equating the migration velocity of an aggregate to that of a spherical particle having the same mobility diameter $d_m$ to obtain the number N of primary particles in the aggregates; determining the fraction of aggregates $\eta_{agg}$ that are singly electrically charged by the analyzer; and estimating the number of aggregates in the volume of gas $n_{agg}$ from the counted total number of aggregates $n_{sph}$ and the charge fraction $\eta_{agg}$.

In another embodiment disclosed herein, a method of estimating the surface area of nanoparticle aerosol aggregates in a gas having a primary particle size a using a differential mobility analyzer for measuring spherical particles comprises estimating the number of aggregates $n_{agg}$ in the gas; and estimating the surface area of the aggregates $A_{agg}$ using the expression:

$$A_{agg}(d_m) = \eta_{agg}(d_m) N(d_m) 4\pi a^2.$$

In a further embodiment disclosed herein, a method of estimating the surface area of nanoparticle aerosol aggregates in a gas having a primary particle size a using a differential mobility analyzer for measuring spherical particles comprises estimating the number of aggregates $n_{agg}$ in the gas; and estimating the surface area of the aggregates $A_{agg}$ using the expression:

$$A_{agg}(d_m) = \eta_{agg}(d_m) N(d_m) 4\pi a^2.$$

These and other features and advantages will become further apparent from the detailed description and accompanying figures that follow. In the figures and description, numerals indicate the various features, like numerals referring to like features throughout both the drawings and the description.

DETAILED DESCRIPTION

Figure 1:
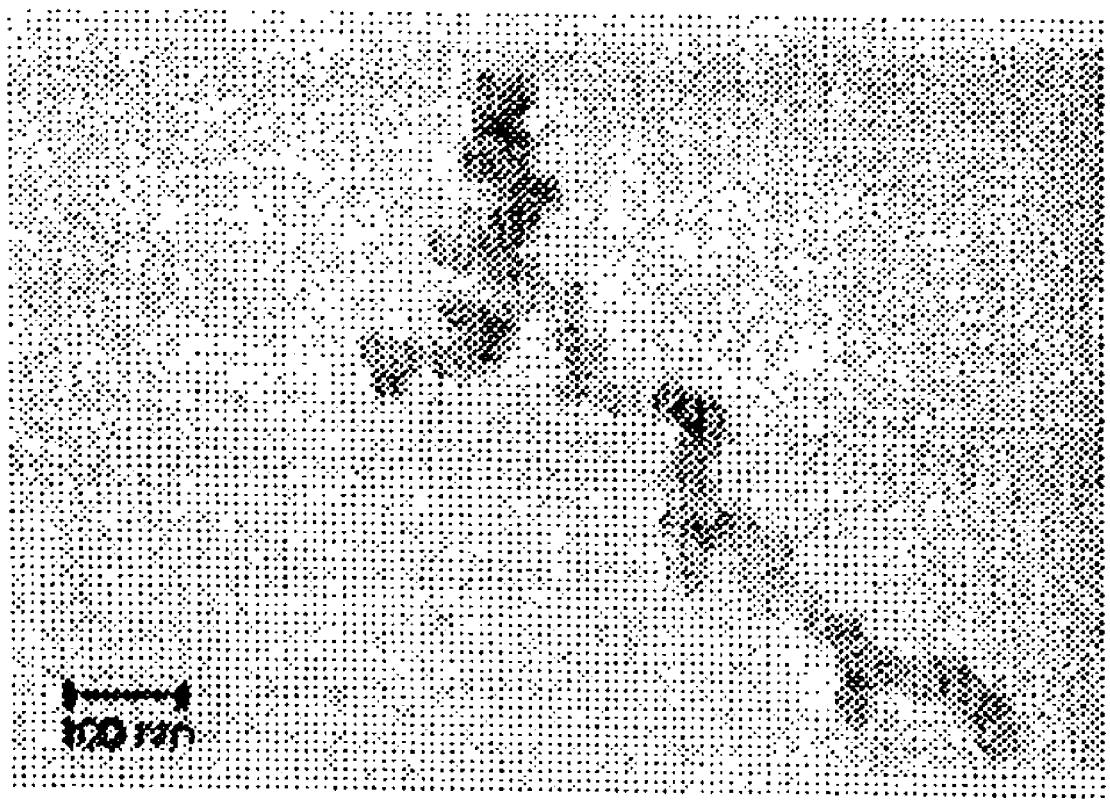
FIG. 1 is a transmission electron micrograph of an atmospheric aggregate sampled with a low pressure impactor.

Briefly, a novel method is disclosed for the online measurement of the number distribution of nanoparticle aerosol aggregates, the surface area distribution of those aggregates and their volume distribution. The method relates the number and size of primary particles that compose the aggregates and the aggregate mobility diameter. The number distribution of nanoparticle aggregates is obtained by calculations based on the drag on the aggregates and the aggregate charging efficiency. The aggregate surface area and volume are obtained by summing over the surface areas and volume of the primary particles that compose the aggregate. The aggregate surface area and volume distribution is then obtained by multiplying the aggregate surface area, volume and the aggregate number distribution. The theoretical analysis was tested experimentally using silver aggregates generated by an evaporation-condensation method. Good agreement is obtained between aggregate number distribution based on theory and the values measured for spheres of sintered aggregates. This good agreement between theoretical and measured values also indicates that the peak aggregate volumes based on theory were accurate to within about 5%. A separate experimental test of the theory was made using data reported in the literature for diesel aggregates. Aggregate volumes calculated from theory were also in good agreement with the aggregate volumes measured by transmission electron microscope analysis.

Nanoparticle chain aggregates are important in technical applications such as the manufacture of fine powered materials. While differential mobility analyzers are frequently used for on-line measurement of aerosol size distributions in the nanoparticle range, the analyzers are usually calibrated for spherical particles. Because nanoparticle aerosol aggregates have a complex morphology when differential mobility diameter data is used directly to obtain surface area and volume distributions for these aggregates, the numbers obtained have significant errors (Xiong, C., and Friedlander, S. K., "Morphological Properties of Atmospheric Aerosol Aggregates", Proc. Nat. Acad. Sci. U.S.A. 98, 11851 (2001)).

Under certain idealized conditions aggregate number, surface area and volume distributions with respect to the mobility diameter can be obtained directly from electrical mobility measurements. The basic assumptions utilized in developing the embodiments disclosed herein are:

1. Nanoparticle aerosol aggregates are composed of primary particles all of which have the same known diameter.

2. The primary particles that compose these aggregates are much smaller than the mean free path of the surrounding gas. This corresponds to Knudsen numbers Kn $$Kn = \lambda a \gg 1 \quad (1)$$

where $\lambda$=mean free path of the gas and a=primary particle radius. In many cases, the limit can be taken as $Kn \geq 10$.

3. The total surface area of an aggregate can be obtained by summing over all primary particles in the aggregate. This provides the maximum surface area which ignores the reduction due to necks between the primary particles.

4. Aggregates are "transparent," that is, (nearly) all surfaces are directly exposed to collisions with molecules from the surrounding gas. This is an acceptable approximation for aggregates with fractal dimensions less than about two.

5. Two singly charged particles, an aggregate and a sphere, trace the same path in the classifier if their migration velocities are equal; both are said to have the same mobility diameter. The Brownian diffusive spread is neglected.

6. Only ultrafine aerosol particles enter the mobility analyzer. Larger particles are removed by a device (e.g., impactor) upstream of the mobility analyzer.

With reference to FIG. 1, a transmission electron microscope (TEM) image of an atmospheric nanoparticle aerosol aggregate is depicted. The properties of the aggregate can be compared with those of the idealized aggregate listed above. The atmospheric aggregate has a low fractal dimension, $D_f$=1.44 and nearly all primary particles are directly exposed to the surroundings. As a result, the aggregate is nearly "transparent." The primary particles have nearly uniform diameters $\approx$27.8 nm, corresponding to a Knudsen number of about 5. This is smaller than $Kn \geq 10$ often taken to be the free molecular regime. The aggregate surface area can be obtained by summing the surface areas of the primary particles. However, this aggregate shows significant necking between the primary particles which would reduce the aggregate surface area, compared to an idealized aggregate.

An analysis of the drag and charge on idealized aggregates as defined by the assumptions listed above is presented below. Based on this analysis, it is possible to determine number, area and volume distributions for the aggregates as a function of mobility diameter for idealized aggregates.

A two module approach may be adopted for calculating aggregate surface areas and volumes: one module for the drag on the aggregates and the other module for aggregate charging efficiency. For $D_f \leq 2$, the drag (Chan, P., and Dahneke, B., "Free-Molecule Drag on Straight Chains of Uniform Spheres", J. Appl. Phys. 52, 3106 (1981)) and the charge (Wen, H. Y., Reischl, G. P., and Kasper, G., "Bipolar Diffusion Charging of Fibrous Aerosol Particles-I. Charging Theory", Aerosol Sci. 15, 89 (1984)) on nanoparticle aerosol aggregates are determined by the number and size of primary particles in an aggregate. Thus, the mobility of an aggregate in an electric field can, in principle, be determined from the number and size of the primary particles that compose the aggregates. The primary particle size is easily measured by electron microscopy. In this analysis, the number of primary particles in an aggregate was first related to the size of a spherical particle with the same mobility diameter by equating their migration velocities in an electric field. Next, using the number and size of the primary particles in an aggregate with a given mobility, the fraction of aggregates that are charged can be determined (Wen, H.Y., Reischl, G. P., and Kasper, G., "Bipolar Diffusion Charging of Fibrous Aerosol ParticlesI. Charging Theory", Aerosol Sci. 15, 89 (1984)). The number distribution for aggregates can then be obtained from the particle counts at the exit from the electrical mobility analyzer. Because the number and size of primary particles for an aggregate having a given mobility is known, the maximum aerosol surface area can be determined by summing over the surface areas of the primary particles. The surface area reduction caused by necking between the particles is ignored. Similarly, the volume distribution can be obtained by summing over the volume of the primary particles. This results in the surface area and volume distributions being obtained from the electrical mobility distribution data.

Regarding Module 1 (for the drag on aggregates), the migration velocity of a particle is a function of its size and is proportional to the drag force F experienced by the particle in an electric field (Friedlander, S. K., "Smoke, Dust and Haze: Fundamentals of Aerosol Dynamics", Oxford University Press, New York (2000)):

$$F = ieE = fc_e \quad (2)$$

where i is the number of electronic charges on a particle, E is the electric field intensity, e is the electronic charge, $c_e$ is the electrical migration velocity, and f is the friction coefficient.

For spherical particles, the friction coefficient is given by Friedlander (Friedlander, S. K., "Smoke, Dust and Haze: Fundamentals of Aerosol Dynamics", Oxford University Press, New York (2000)) as:

$$f = \frac{3\pi\mu d_m}{C(d_m)} \quad (3)$$

where $\mu$ is the gas viscosity, $d_m$ is the mobility diameter, and C is the slip correction coefficient.

Chan, P., and Dahneke, B. ("Free-Molecule Drag on Straight Chains of Uniform Spheres", J. Appl. Phys. 52, 3106 (1981)) used Monte Carlo computations to calculate the drag on the basic chain units (BCD) composed of two primary particles. They calculated the total drag on the aggregate by adding the drag over all the BCU present in the straight chain aggregate:

$$F = (c^*(N-1) + c^*_{sph})\mu a c_e/Kn \quad (4)$$

where N is the number of primary particles, $c^*$ is the dimensionless drag force and $c^*_{sph}$ is the dimensional drag force experienced by a single sphere, accounting for the presence of the two hemispherical end caps. When the aggregate orientation is random, the value of $c^*$ is approximately 9.34 for diffuse reflection and approximately 6.85 for specular reflection. Dabneke, B., "Viscous Resistance of Straight-Chain Aggregates of Uniform Spheres", Aerosol Sci. Tech. L 179 (1982) assumed 7% specular reflection and 93% diffuse reflection to calculate the total drag. This leads to $c^* = 9.17$ for aggregates with random orientation. For N>12, Eq. (4) can be approximated to within 1% accuracy by Eq. (5)

$$F = c^*N\mu a c_e/Kn \quad (5)$$

This result is based on the low velocity limit (aggregate velocity <<mean molecular velocity) for the drag on aggregates composed of primary particles that are much smaller than the mean free path of the gas. Eq. 5 is presumed to hold for aggregates that have occasional branches and kinks (Chan, P., and Dahneke, B., "Free-Molecule Drag on Straight Chains of Uniform Spheres", J. Appl. Phys. 52, 3106 (1981)).

There is experimental support for the computations of Chan, P., and Dahneke, B. Kasper, G. ("Dynamics and Measurement of Smokes. II The Aerodynamic Diameter of Chain Aggregates in the Transition Regime", Aerosol Sci. Tech. 1, 201 (1982)) measured the slip coefficients of $Fe_2O_3$ chain aggregates with 10 to 100 primary particles in the transition regime (17.5 nm<a<60 nm). He compared his experimental results with the calculations in the Dahneke, B. 1982 reference which were based in part on the Chan, P., and Dahneke, B. 1981 reference.

To relate migration velocity and mobility diameter, a nanoparticle aerosol aggregate and a spherical particle were considered to have a single unit electrical charge. If the two have the same migration velocity, with F in Eq. (2) given by Eq. (5) for the aggregate, then f in Eq. (3) for the sphere gives:

$$\frac{d_m}{C(d_m)} = \frac{c^*Na^2}{3\pi\lambda} \quad (6)$$

Figure 2:
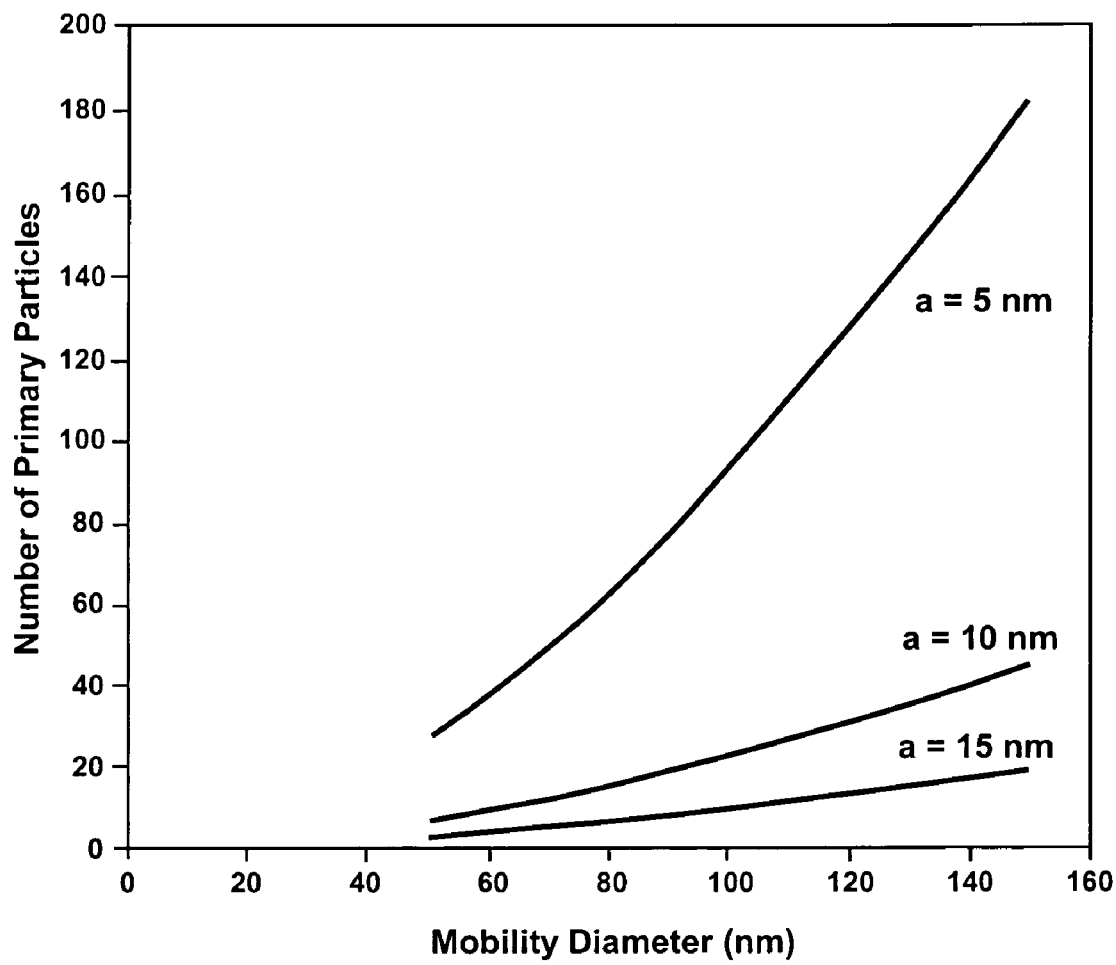
FIG. 2 is a graph showing the number of primary particles in an aggregate as a function of mobility diameter for primary particle diameters of 5, 10, and 15 nm.

For $D_f \leq 2$, the mobility diameter is independent of the fractal dimension of the aggregate. Using Eq. 6, the number of primary particles in an aggregate with primary particle size in the free molecular regime can be related to the mobility diameter of a sphere that can lie in the transition regime (Kn~1). The number of primary particles is shown as a function of mobility diameter in FIG. 2.

In the analysis explaining Module I, where the migration velocity of the aggregate and sphere were equated, it was assumed that both carried a unit charge. However, the fraction of spheres and aggregates that assume unit charge differ. Expressions for calculating the charge distributions are needed for both. Thus, a first presumption for Module 2 (charging efficiency) has the spheres charging in a bipolar diffusion charger.

The charging efficiency is the fraction of the particles of a given size that have a certain number of charges at equilibrium. Wiedensohler A., "An Approximation of the Bipolar Charge Distribution for Particle in the Submicron Size Range", J. Aerosol Sci. 19, 387 (1988) developed a fast numerical technique to calculate the fraction of spherical particles carrying up to 2 charges. This technique is widely used to calculate the charging efficiency in commercial differential mobility analyzers (DMA) software. The fraction of spherical particles carrying three or more charges is given by Gunn, R., "The Ratio of the Positive and Negative Light Ion Conductivities within a Neutral Aerosol Space", J Colloid Sci. 11, 661 (1956).

In their analysis of aggregate charging, Wen, H.Y., Reischl, G. P., and Kasper, G., "Bipolar Diffusion Charging of Fibrous Aerosol Particles-I. Charging Theory", Aerosol Sci. 15, 89 (1984) approximated aggregate structure by long prolate spheroids. They introduced a lumped parameter comprising the charging equivalent diameter for a given number and size of the primary particles in an aggregate. The length of the minor axis of the prolate spheroids was approximated by the diameter of the primary particles. For straight chain aggregates, the length of the major axis is the sum of the diameters of all the primary particles. The aspect ratio can thus be approximated by the total number of primary particles. According to their analysis for bipolar diffusion charging, the Boltzmann distribution is a good approximation for the fraction of aggregates with one charge q:

$$\eta_{agg} = \frac{e}{(\pi D_{qe}kT)^{1/2}} \exp\left[\frac{-q^2e^2}{D_{qe}kT}\right] \quad (7)$$

where $D_{qe}$ is the charging equivalent diameter of the aggregate:

$$D_{qe} = \frac{2aN}{\ln(2N)} \quad (8)$$

The measurements of Wen, H. Y., Reischl, G. P., and Kasper, G., "Bipolar Diffusion Charging of Fibrous Aerosol Particles-II Charging and Electrical Mobility Measurements on Linear Chain Aggregates", J Aerosol Sci. 15, 103 (1984)

showed that Eq. 7 is a good approximation for the charge on chain aggregates to within about 10%. These results were based on experiments with flame generated $\gamma$-$Fe_2O_3$ chain aggregates with primary particle radius between 20.5 and 40.5 nm.

Figure 3:
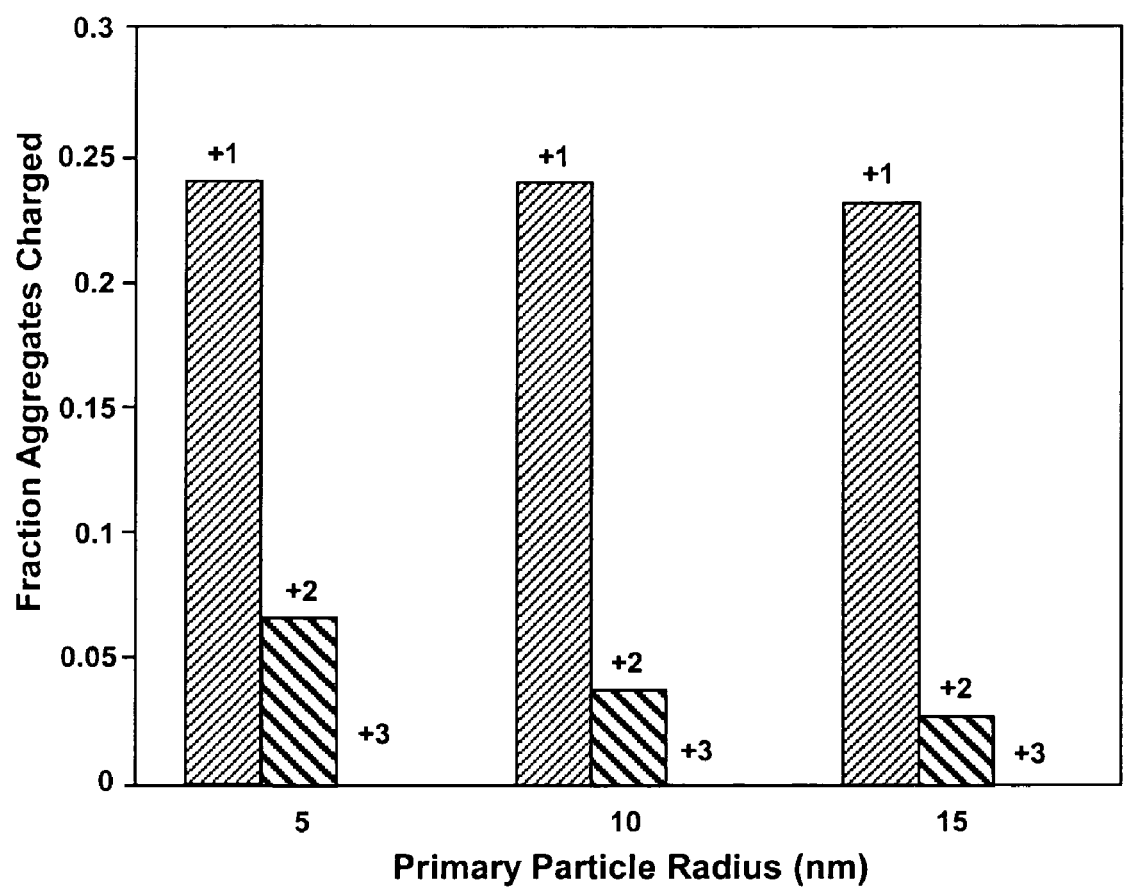
FIG. 3 is a graph comparing the fraction of aggregates which are single, double or triple charged for primary particle radii of 5, 10, and 15 nm and a mobility diameter of 80 nm.

FIG. 3, based on Eqs. 7 and 8, compares the fraction of charged aggregates composed of primary particles with radii of 5, 10 and 15 nm for nanoparticle aerosol aggregates with a mobility diameter of 80 nm. The charging efficiency (fraction charged) is shown for singly, doubly, and triply charged aggregates. Similar behavior of the charging efficiencies is expected for other mobility diameters. The fraction of the aggregates that are multiply charged decreases with increase in primary particle size. One might expect aggregate charging efficiency to increase with primary particle size. However, FIG. 3 shows that even though the mobility diameter is the same in the three cases (primary particle radii 5, 10, 15 nm), the number of primary particles is not the same. In this case the larger primary particle sizes correspond to the aggregates with fewer primary particles and this leads to a decrease in charging efficiency.

Eqs. 6 and 8 can be combined to eliminate N and give $D_{qe}$ in terms of the mobility diameter for a given primary particle size. Thus, the charge distribution for aggregates (Eq. 7) can be determined as a function of the mobility diameter. The number distribution obtained from the mobility analyzer can then be corrected for aggregate charging efficiency as described below.

Figure 4:
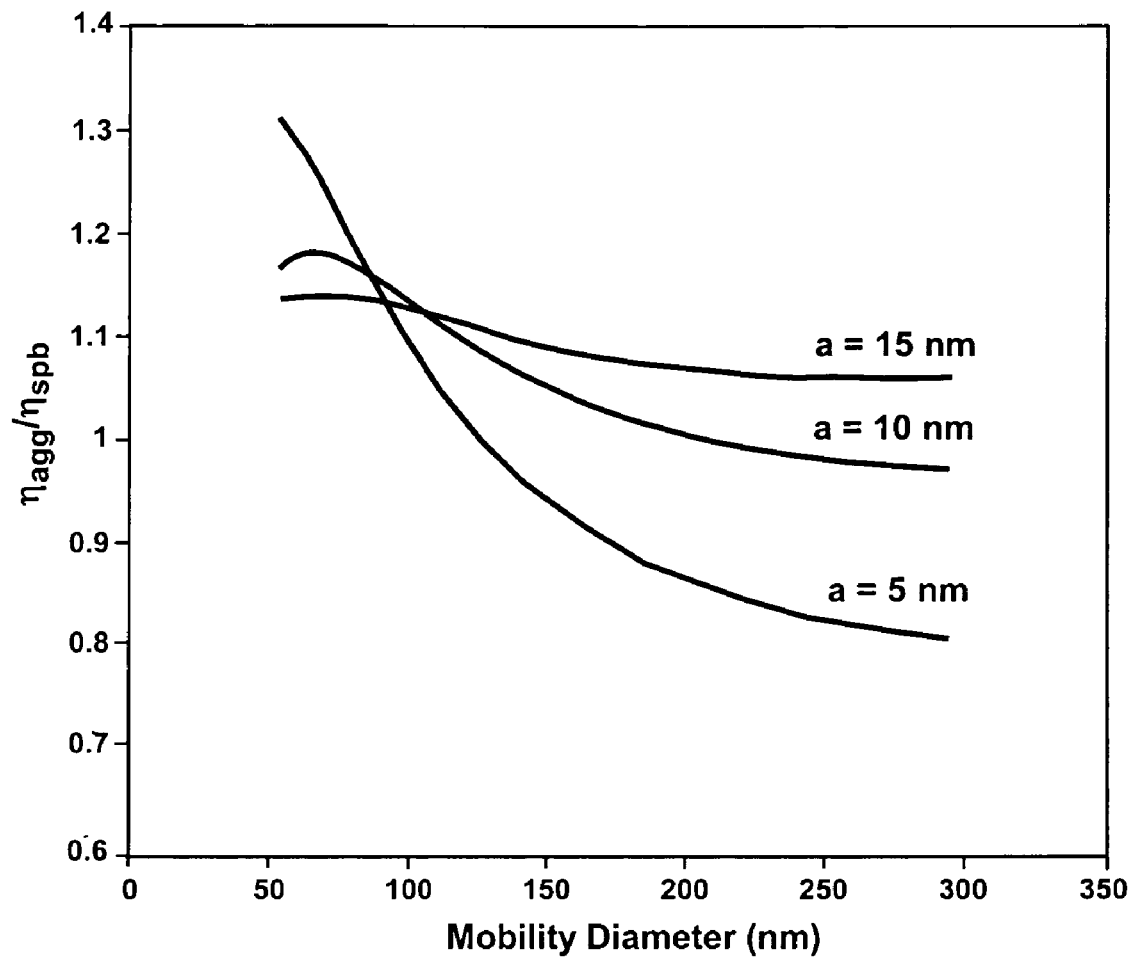
FIG. 4 is a graph showing the charging efficiency of a singly charged sphere.

A comparison of the charging efficiencies of nanoparticle aerosol aggregates carrying unit charge with that of spheres of equivalent mobility diameter is shown in FIG. 4 with primary particle size as a parameter. Mobility diameters between 50 and 250 nm and three primary particle radii of 5, 10 and 15 nm (in the range for atmospheric aggregates, for example) are considered. As shown in FIG. 4 the charging efficiencies of nanoparticle aerosol aggregates carrying unit charge are similar (but not equal) to those of spheres with the same mobility diameter.

To calculate the number distribution of nanoparticle aerosol aggregates, it must first be noted that only a fraction of the aggregates that are charged pass through the mobility analyzer. For the case of singly charged spheres or aggregates, the true number concentration of spheres or aggregates can be obtained by correcting for their charging efficiencies. For a given number of spheres or aggregates that are detected at the exit from the mobility analyzer per unit volume, the true number concentrations of aggregates and spheres will differ because of different charging efficiencies. The corresponding number distribution functions are related by the expression:

$$n_{agg} = n_{sph} \frac{\eta_{sph}}{\eta_{agg}} \quad (9)$$

where, $n_{sph}$ and $n_{agg}$ are the number distribution for spheres and aggregates, respectively, and $\eta_{sph}$ and $\eta_{agg}$ are the fraction of singly charged spheres and aggregates (Eq. 7), respectively. Multiple charging (FIG. 3) can be taken into account using methods proposed by Hoppel, W. A, "Determination of the Aerosol Size Distribution from the Mobility Distribution of the Charged Fraction of Aerosols", J Aerosol Sci. 9, 41 (1978); Plomp, A., Brink, H. M., Spoelstra, H. and van de Vate, J. F., "A High Resolution Electrical Mobility Aerosol Spectrometer", J Aerosol Sci. 14, 363 (1982) and Fissan, H., Helsper, C., and Thielen, H. J., "Determination of Particle Size Distribution by means of an Electrostatic Classifier", Aerosol Sci. 14, 354 (1982).

The surface area distribution ($A_{agg}$) with respect to the mobility diameter can be obtained from the number distribution for aggregates from the expression:

$$A_{agg}(d_m) = n_{agg}(d_m) N(d_m) 4\pi a^2 \quad (10)$$

where $N(d_m)$ can be obtained from Eq. 6. The accessible area may be less than the sum of the surface area of the primary particles due to the shielding effects of the exterior primary particles. Based on the assumption that the aggregates are transparent, the accessible surface area is likely to be close to the total surface area of the primary particles for DJ<2 (Rosner, D. E. and Tandon, P., "Prediction and Correlation of Accessible Area of Large Multiparticle Aggregates", AIChEJ 40, 1167 (1994)).

The volume distribution $V_{agg}$ with respect to the mobility diameter is then obtained from the expression:

$$V_{agg}(d_m) = n_{agg}(d_m) N(d_m) \left( \frac{4\pi a^3}{3} \right) \quad (11)$$

To compare the surface area of the aggregates with that of spheres with the same mobility diameter, the case in which a given number of particles (spheres or aggregates) per unit volume are detected at the exit from the mobility analyzer is considered. For this number, the ratio of the maximum total surface area of aggregates (Eq. 10) to the surface area of spheres is:

$$R_a = \frac{N(4\pi a^2)}{\pi d_m^2} \frac{n_{agg}}{n_{sph}} = \frac{N(4\pi a^2)}{\pi d_m^2} \frac{\eta_{sph}}{\eta_{agg}} \quad (12)$$

The value of N in Eq. 12 is a function of mobility diameter. Using Eq. 6, Eq. 12 can be written as:

$$R_a = \left( \frac{d_m}{C(d_m)} \frac{3\pi\lambda}{c^*} \right) \frac{4}{d_m^2} \frac{\eta_{sph}}{\eta_{agg}} \quad (13)$$

Figure 5:
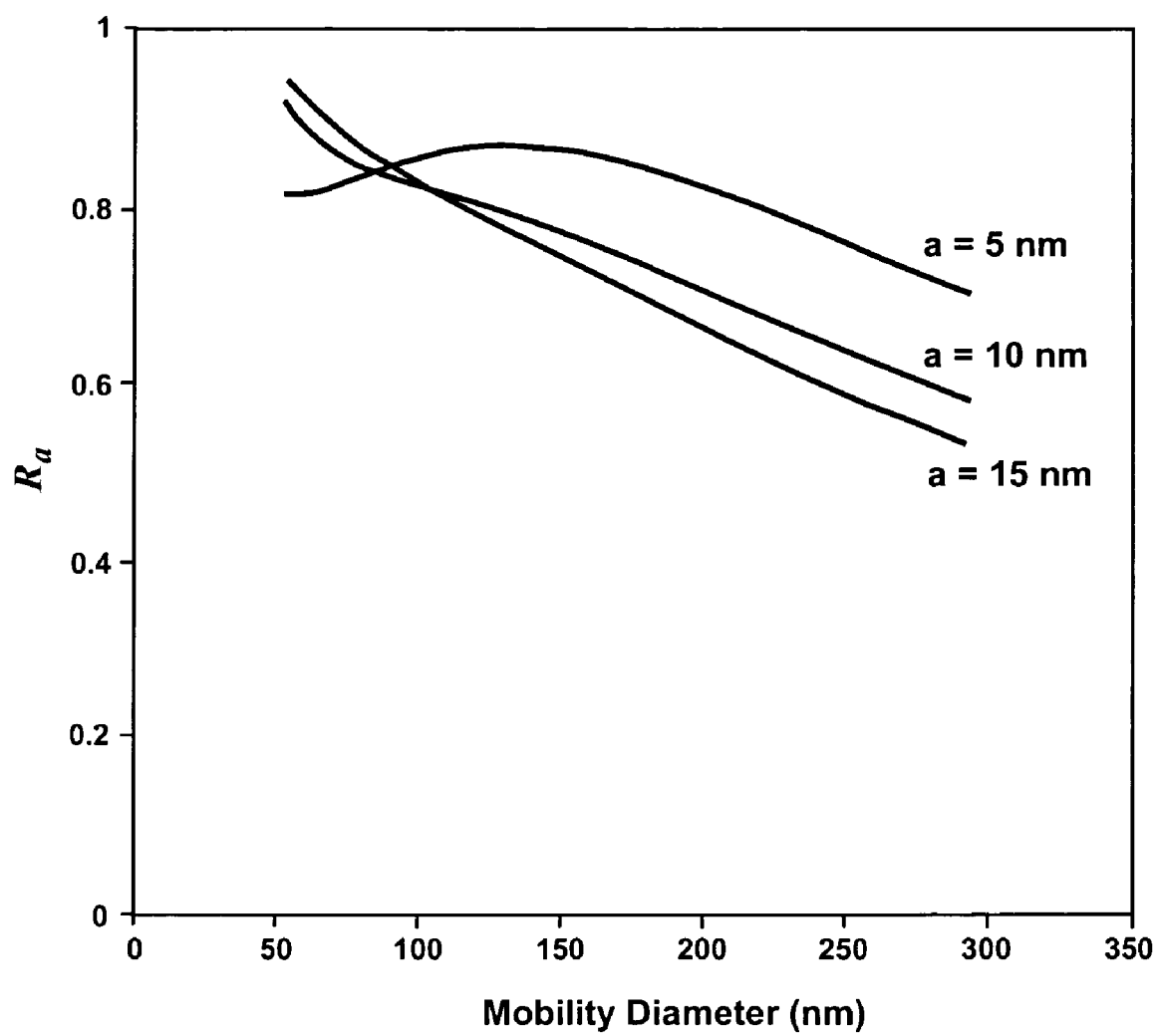
FIG. 5 is a graph showing the ratio of surface area of an aggregate to that of a sphere with the same migration velocity as a function of mobility diameter.

$R_a$ is a weak function of primary particle size through the charging efficiencies. As shown in FIG. 4, the ratio of charging efficiencies is approximately unity at room temperature. FIG. 5 shows $R_a$ as a function of mobility diameter with the primary particle size as a parameter. $R_a$ is shown to decrease with increasing mobility diameter. FIG. 5 shows that over the mobility range considered, the surface area of the aggregates is somewhat over predicted by the calculations based on their mobility diameter.

Figure 6:
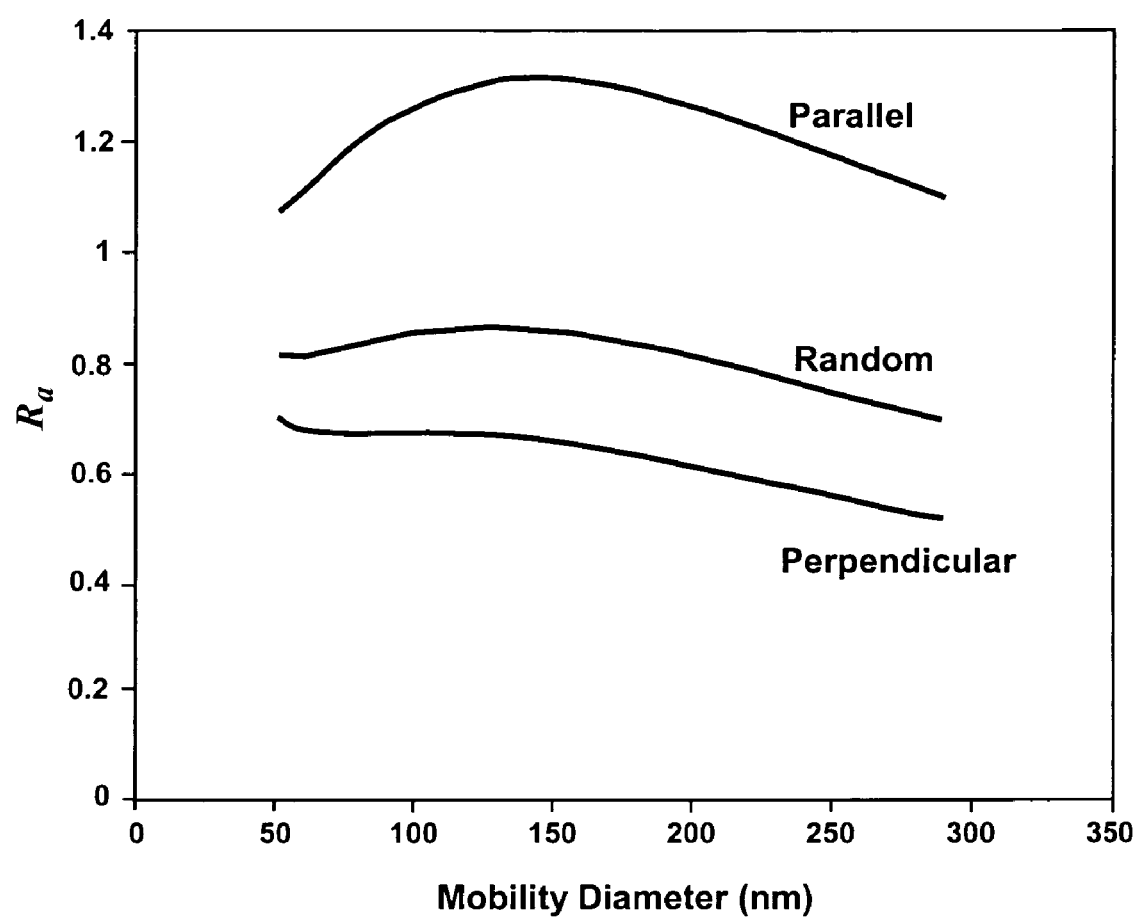
FIG. 6 is a graph showing the ratio of surface area of an aggregate to that of a sphere with the same migration velocity, as a function of mobility diameter, for parallel, random and perpendicular orientations with respect to the aggregate motion relative to the gas.

The effect of aggregate orientation on calculated surface area is shown in FIG. 6 for parallel, perpendicular and random orientation with respect to the aggregate motion relative to the gas. The direction of aggregate motion relative to the gas is parallel to the electric field. Parallel orientation to the aggregate relative motion may be caused by aggregate dipole formation and subsequent alignment with the electric field (Stöber W., Boose C. and Prodi V. (1974) Uber die Orientierung und den Dynamischen Formfaktor von Kettenformigen Aerosolteilchen in Ladungsspektrometern. Water, Air Soil Pol/ut. 3, 493). The effect of orientation is incorporated in the analysis through c*. Values of c* for these orientations are given by Dahneke, B., "Viscous Resistance of Straight-Chain Aggregates of Uniform Spheres", Aerosol Sci. Tech. L 179 (1982). Calculations based on mobility diameter somewhat over predict the aggregate surface area for random and perpendicular orientations, but under predict for parallel orientation.

The ratio of the total volume of aggregates to that of spheres (Eq. 10) having the same mobility diameter can be written as $$R_v = \frac{N\left(\frac{4\pi a^3}{3}\right)}{\frac{\pi d_m^2}{6}} \frac{\eta_{sph}}{\eta_{agg}} \quad (14)$$

Figure 7:
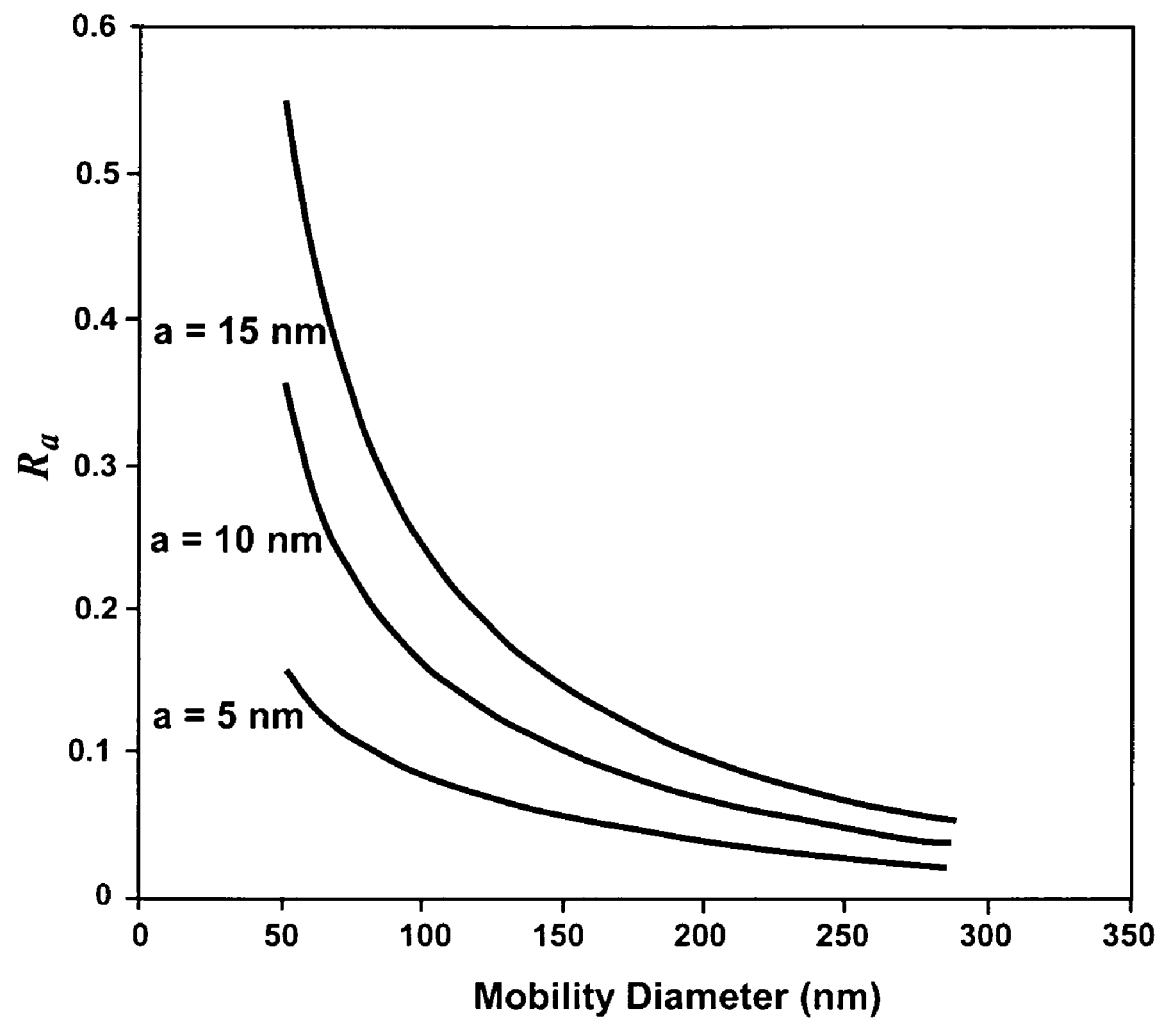
FIG. 7 is a graph showing the ratio of volume of an aggregate to that of a sphere having the same migration velocity as a function of mobility diameter.

FIG. 7 shows $R_v$ as a function of mobility diameter with primary particle size as a parameter. The most striking result is that for any primary particle size, the volume of an aggregate is much less than the volume of a mobility equivalent sphere. Thus, the volume (or mass) distribution based on the assumption of spherical particles grossly over predicts the volume (or mass) distribution for the aggregates.

The above discussion applies to the case of aggregates with primary particle sizes much smaller than the mean free path. This assumption considerably simplified the analysis and makes use of established correlations available in the literature. For larger primary particles, corresponding to the transition regime, analysis of aggregate behavior is much more complex (Dahneke, B., "Viscous Resistance of Straight-Chain Aggregates of Uniform Spheres", Aerosol Sci. Tech. L 179 (1982); Rogak, S. N., Flagan, R. C., and Nguyen, H. V., "The Mobility and Structure of Aerosol Agglomerates", Aerosol Sci. Technol. 18, 25 (1993).

The method holds for idealized aggregates with low fractal dimension and uniform primary particles in the free molecule size range. Particles of equal migration velocities will trace similar paths in the mobility analyzer and have the same mobility diameter (neglecting Browning diffusive speed). As described above, the method uses two modules, one for the drag on the aggregates and the second for the aggregate charging efficiency. As set forth above, Module 1 relates the number (N) and the radius (a) of primary particles that compose the aggregates to the mobility diameter ($d_m$). The relation shown in Eq. (6) is obtained by equating the migration velocity of the aggregates to that of spheres with the same mobility diameter where, λ is the mean free path of the gas. The value of c* is equal to 6.62 for aggregates with orientation parallel to the gas flow. For a given primary particle size, aggregate volume and surface area can be obtained from Eq. 6 by summing the surface areas and volumes of all the primary particles in the aggregate, respectively.

Module 2 combines Eq. 6 with the aggregate charging efficiency (different from that of spheres) to obtain the aggregate number distributions. The aggregate surface area (and volume) distribution is obtained by multiplying the aggregate surface area (and volume) and the aggregate number distribution. The use of this technique shows that prior techniques using calibration based on spherical particles resulted in a surface area distribution for aggregates with random orientation that was slightly greater than predicted. However the volume distribution was greatly over predicted by about a factor of 10.

Experimental data in support of the module theory is set forth below. For these tests, the aggregate volume (Module 1) and the aggregate number distribution (Module 2) were compared with the experimental values. Silver aggregates generated by an evaporation-condensation method are used as the test aerosol. Literature data for diesel aggregates (Park et al., 2004) are also used to compare theoretical aggregate volumes with values measured independently by transmission electron microscopy (TEM).

To test aggregate number distributions, silver nanoparticle aggregates were generated by an evaporation-condensation method. The aggregates were sintered at 400° C. to obtain spheres with the same volume as the original aggregates, with the assumption that the aggregate volume does not change upon sintering and coagulation can be neglected. Thus the number of aggregates in a given volume range (number-volume distribution, dN/d log v) should not change after sintering to the spheres. The number distributions (dN/d log v) of the spheres were measured using commercially available aerosol instrument manager software (AIMS). There is good agreement between the aggregate number-volume distribution based on theory and the values obtained for sintered volume equivalent spheres from AIMS.

The number of aggregates in a given volume range (number-volume distribution, dN/d log v vs v) were compared with the number-volume distribution of volume equivalent spheres formed after sintering. It was assumed that the aggregate volume (v) does not change after sintering to spheres and the number-volume distribution of the spheres is unchanged. Therefore, the aggregate number-volume distribution should be the same as that of volume equivalent spheres formed after sintering. The comparison can be used to test Eq. 6 and the aggregate number distribution obtained from the theoretical analysis above.

For this purpose, the silver aggregates were generated by the evaporation-condensation technique of Weber A. P. and Friedlander, S. K., "In situ determination of the activation energy for restructuring the of nanometer aerosol agglomerates.", J. Aerosol Sci. 28, 179 (1997). The aggregates were then heated to 400° C. to obtain spherical particles with the same volume. The number-size distribution of spheres was obtained from Aerosol Instrument Manager Software (AIMS) and was converted to number-volume distribution and the aggregate number-size distribution (dN/d log $d_m$ vs $d_m$) was obtained. The method involved use of the aggregate charging efficiency (assumed true based on the 1984 Wen et al. reference) and Eq. 6. To convert the number-size distribution to number-volume distribution, the aggregate volume can be determined from Eq. 6. Thus if the aggregate number-volume distribution agrees with that of spheres obtained after sintering, then Eq. 6 and the aggregate number distribution can be taken as true.

The basic assumptions include:

1. The aggregate volume does not change upon sintering to a sphere. Aggregates breaking into smaller fragment and coagulations are limited at 400° C.;

2. Silver aggregates align parallel to the aerosol flow;

3. All primary particles of the aggregates are free-molecular and are equal in size; and 4. The fractal dimensions of all the aggregates are less than 2.

Silver aggregates were chosen for this study so that low sintering temperatures can be maintained to minimize coagulation and particle loss due to thermophoresis.

Figure 9:
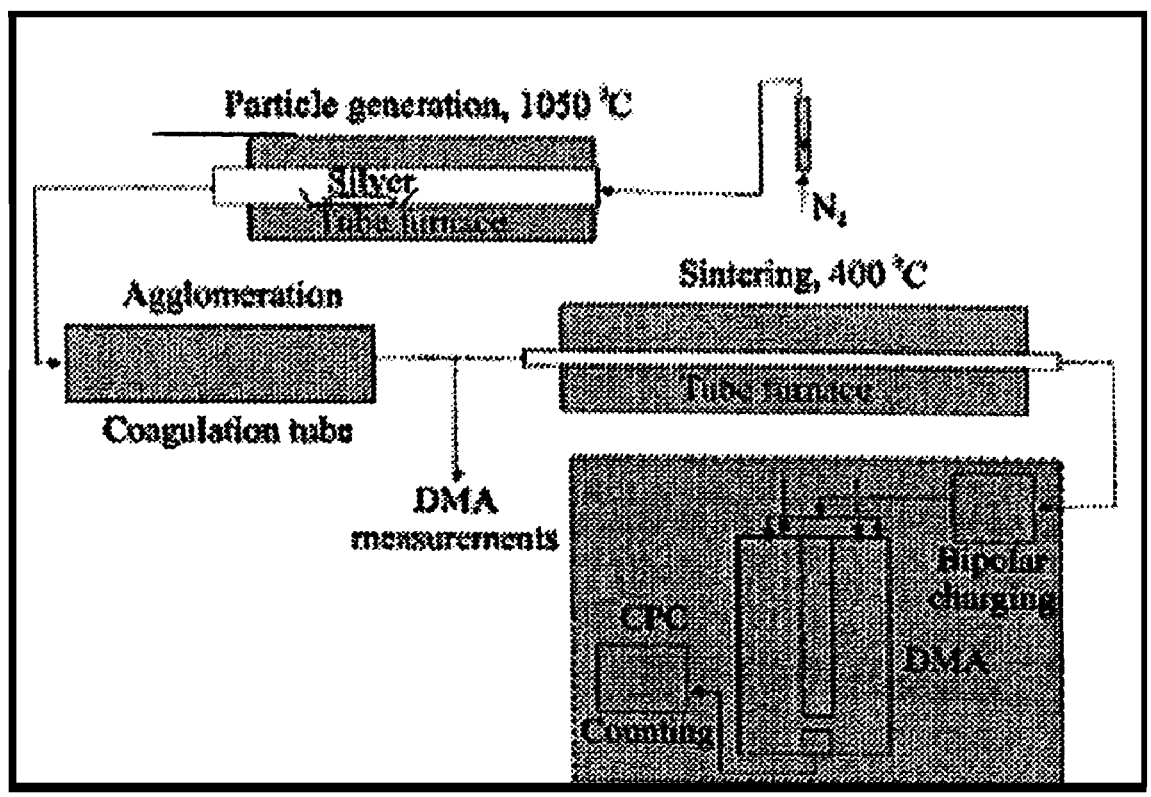
FIG. 9 is a schematic diagraph of the system used to produce silver aggregates.

A schematic diagram of the experimental setup is shown in FIG. 9. Silver nanoparticles were generated by heating bulk silver placed in a ceramic boat inside a tube furnace (Thermolyne Model 21100, length of heating zone=41 cm, with quartz tube (I.D. 2.18 cm)). The boat was placed in the quartz tube near the exit of the furnace. Nitrogen (99.99%) was used as the carrier gas at a flow rate of 1 lpm. The silver was evaporated at 1050° C. into the flowing nitrogen which was then cooled to room temperature at the other end of the furnace. A high cooling rate was maintained at the end of the furnace by cooling the quartz tube in a water bath at room temperature. During cooling, the silver vapor condensed to form spherical primary particles.

The collision-coalescence mechanism of particle growth is thought to control the primary particle diameter in high-temperature processes (Bandyopadhyaya et al., 2004; Friedlander, 2000). Particles initially coalesce upon collision to form larger particles. As the temperature falls, the collision rate becomes faster than the rate of coalescence; the primary particles assumed their final size and aggregates composed of primary particles start to form. To provide sufficient residence time for agglomeration at room temperature, a glass tube (I.D. 6.35 cm and length 131 cm with connections) was placed in line after the cooling section.

Aggregate sintering was carried out in a second tube furnace (Lindberg, Model 54357-A with temperature controller Model 59744-A, length of heating zone=61 cm) at 400° C. inside a glass tube (I.D. 8 mm). The portion of the glass tube at the end of the furnace was cooled to room temperature in a water bath. This provided cooling of the aerosol to room temperature to reduce or stop further aggregation of the sintered aggregates. Mobility data were obtained by a DMA (TSI model 3080) in combination with a condensation particle counter (CPC, TSI Model 3010) which draws the aerosol at 1 lpm by a vacuum pump. To ensure the same flow rates in the furnace and the CPC, a small amount of filtered excess air was introduced into the system through a REPA filter. Mobility measurements were made at the entrance and the exit of the second tube furnace, although not simultaneously.

Samples for TEM analysis were deposited from an aerosol side stream onto a 3 mm diameter copper TEM grid (Electron Microscopy Sciences, 3 mm, carbon film) supported on a filter (Millipore, 0.1 μm) placed inside a filter chamber. The carrier gas passed through the filter. However, only a fraction of the particles passed through the filter, with the remaining particles deposited on the filter and the TEM grid by diffusion. While the morphology of the particles can be obtained by the TEM analysis, size distribution could not be obtained from the TEM analysis because the deposited particles were not a representative sample with respect to the particle size. The sampling time was 20 min.

Figure 10A:
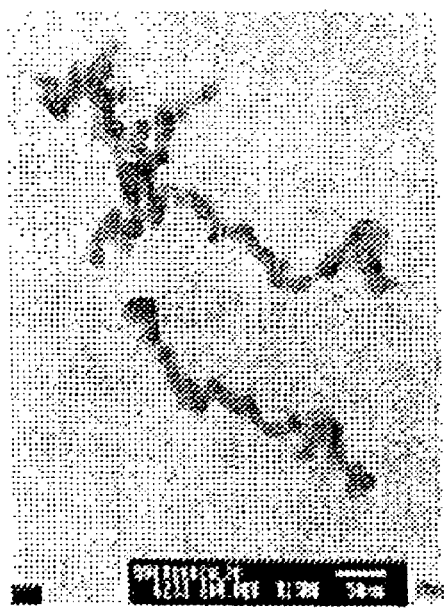
FIGS. 10a and 10b are TEM photographs of typical aggregates produced using the apparatus of FIG. 9.
Figure 10B:

Silver aggregate images from the TEM analysis are shown in FIG. 10. The primary particles were nearly uniform and the average primary particle diameter was about 18.5 nm. The fractal dimension of the aggregate shown in figure in FIG. 10*a* is 1.8. FIG. 10*b* is a low magnification TEM image of the aggregates that shows the aggregates are fairly "transparent", i.e., each primary particle is equally exposed to surroundings. In these experiments, the formation of necks was seen between the primary particles, which is typical for silver aggregates as reported by Weber and Friedlander in the 1997 article. Formation of necks reduces the aggregate surface area to an amount less than the total surface area of all the primary particles.

Due to the high temperature inside the sintering tube, all collisions lead to substantially spherical particles. The residence time in the sintering zone was sufficiently low to cause a significant change in the number distribution with respect to aggregate volume. However, a high quenching rate at the end of the sintering tube was needed to minimize the agglomeration. The TEM images of the particle samples at the end of sintering tube show that the sintering was complete. However, it was observed that a particle loss of up to about 19.5% occurred at the end of sintering tube as a result of thermophoresis. Therefore, the number distributions were normalized. It was assumed that the particle loss due to thermophoresis was size independent and did not significantly affect the normalized number distribution.

Figure 11:
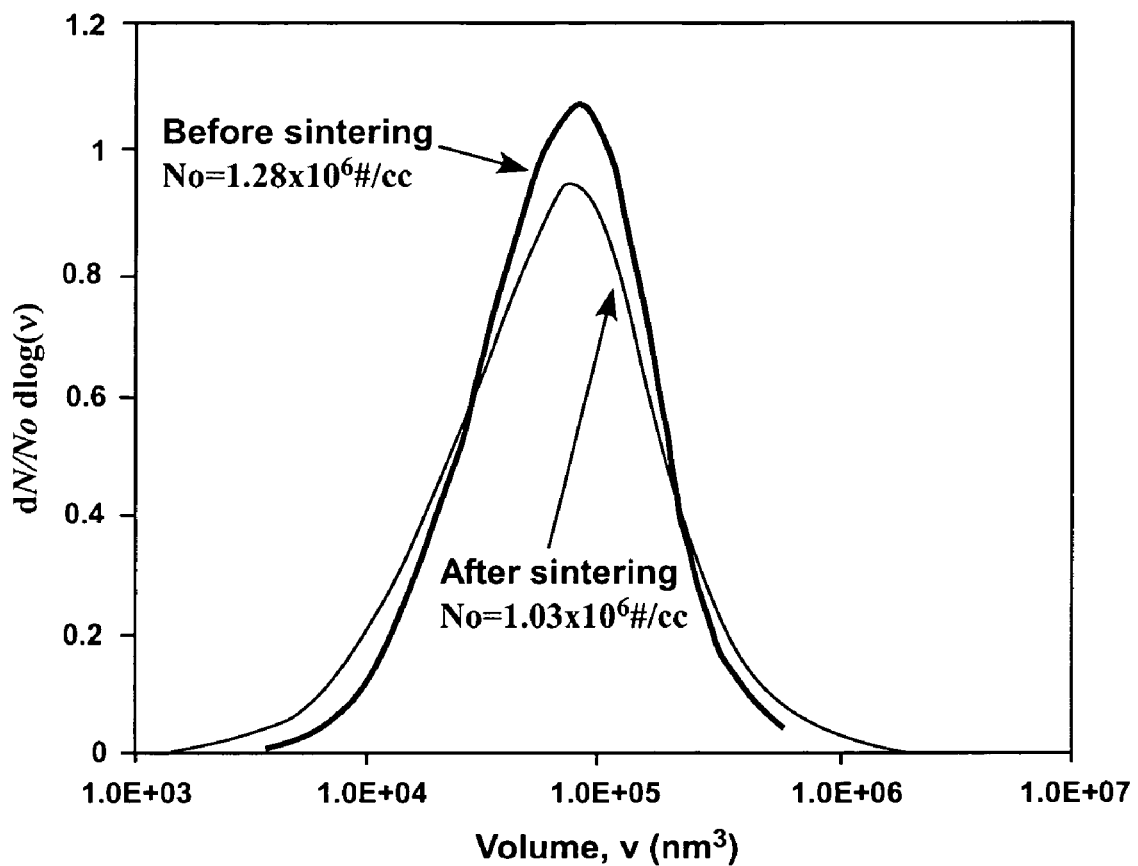
FIG. 11 is a graph comparing normalized number-volume distributions with volume-equivalent spheres.

FIG. 11 shows the normalized number distributions (dN/($N_0$d log v) vs v) of aggregates before and after sintering. Good agreement was found between the normalized aggregate number-volume distribution and that of volume equivalent spheres. The width of distribution and the aggregate volume (X-axis) were compared. The distribution is somewhat wider after sintering and the difference in the peaks of the curves is about 13% which is within experimental error. The aggregate number distribution based on spheres with diameter equal to the mobility diameter was much wider and the difference in peak heights was 31%. The number distribution of the spheres formed after sintering was assumed to be true. As a result, the comparison verifies aggregate normalized number distribution and the validity of Eq. 6. However, due to particle loss, total number of particles before and after sintering cannot be compared to provide additional support for Eq. 6.

Secondly, the peak position of the aggregate number distribution (aggregate volume=$8.34 \times 10^4$ nm$^3$, X-axis) based on the theoretical method described above was in good agreement with that of spheres (aggregate volume=$7.92 \times 10^4$ nm$^3$) obtained after sintering. Based on the assumption that volume is conserved during sintering, this agreement indicates that the calculated peak volume was accurate to within 5%. The peak position for the distribution based on the spheres with diameter equal to the mobility diameter, $d_m$ was $1.87 \times 10^5$ nm$^3$ which is 2.36 times larger than the (more correct) value for the spheres of sintered aggregates. The comparison confirms that the calculation based on spheres with diameter equal to the mobility diameter greatly overpredicts the aggregate volume as shown above.

The aggregate volume (and surface area) distribution is the product of aggregate volume (and surface area) and the aggregate number distribution.

Figure 12:
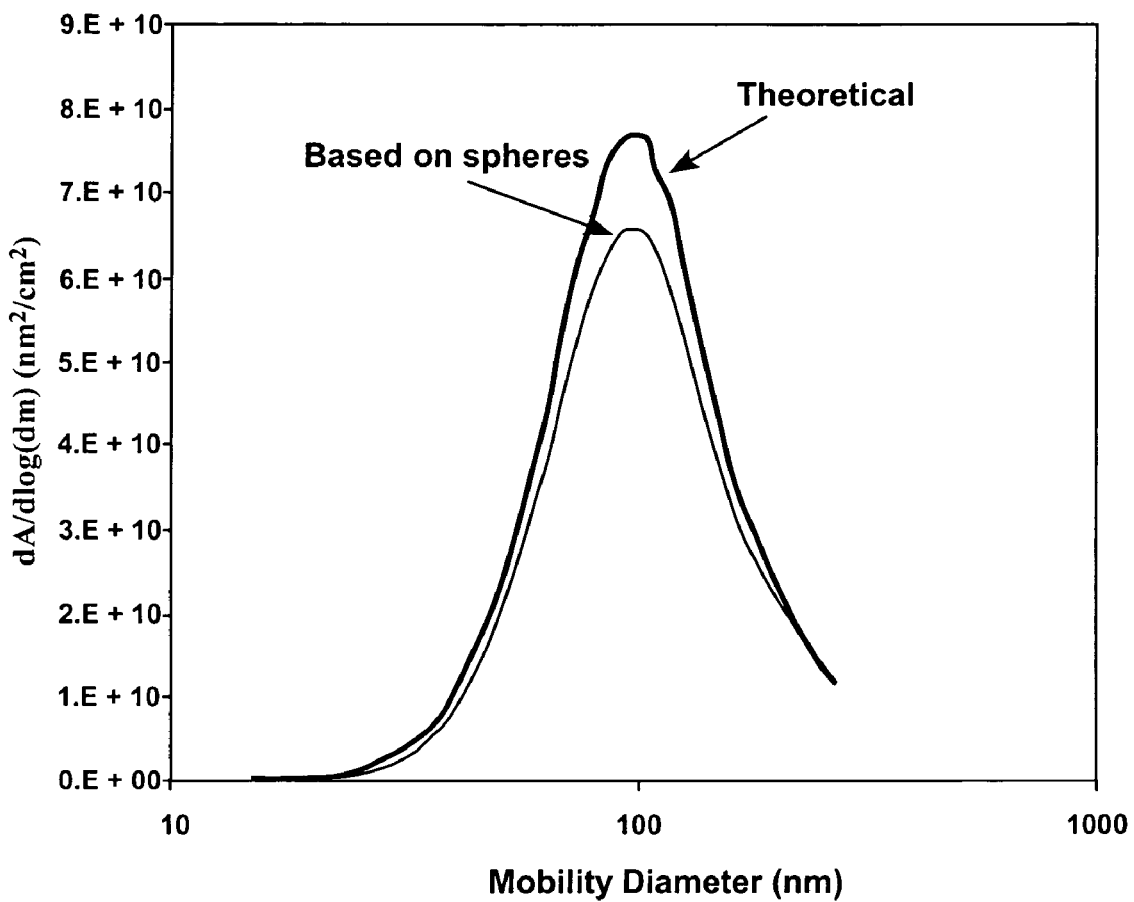
FIG. 12 is a graph comparing calculated surface area distributions based on spheres compared to the theoretical approach.
Figure 13:
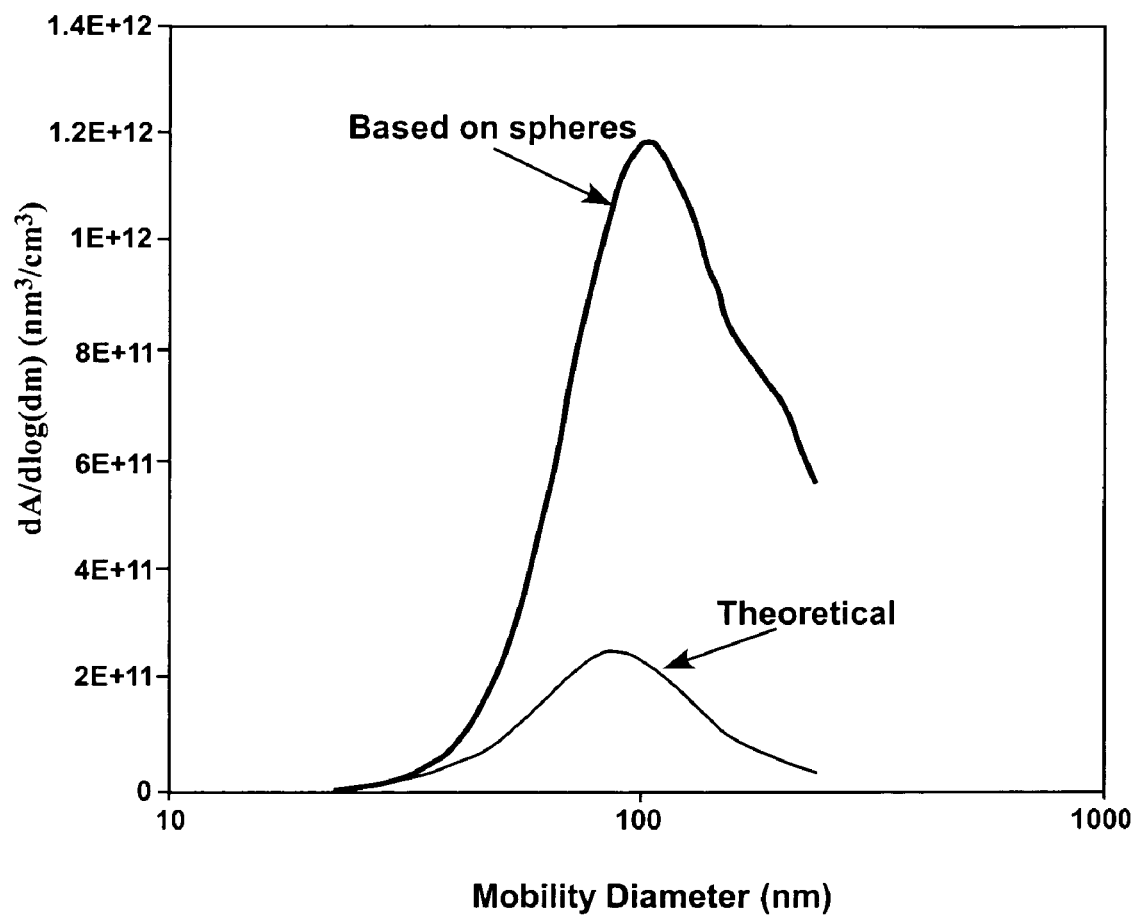
FIG. 13 is a graph comparing calculated volume distributions based on spheres compared to the theoretical approach.

The aggregate surface area and volume distributions based on spheres (from AIMS) and that obtained from the theoretical method described above are shown in FIG. 12 and FIG. 13, respectively. The theoretical approach is more accurate. The aggregate surface area is somewhat greater than that of spheres with the same mobility diameter but the aggregate volumes are much less than that of spheres with the same mobility diameter.

In the above comparison, the primary particle size was obtained from the TEM measurements so that the theoretical method described above could be tested against the experimental data. However, the method is not limited to the use of the primary particle size from an independent measurement such as TEM. The primary particle size can be determined from the DMA-CPC measurements using a trial and error approach as follows.

The total number of particles per unit volume of a given aerosol can be obtained directly from the CPC measurements. The number of particles in a given mobility size range can be obtained by the method described above, if the primary particle size is known. The total number of particles can then be obtained by summing over the entire mobility range for a given aerosol. For an assumed primary particle size, the calculated total number of particles from the mobility analyzer data can be compared with that counted by the CPC. Thus, based on the best agreement between the total particle counts, the primary particle size can be determined by trial and error.

Park et al. referenced above obtained aggregate volume as a function of the mobility diameter. In their studies, the aggregate volume was measured to determine the inherent density of the primary particles in the aggregate. They sampled the aggregates with a given mobility diameter by the low pressure impactor (LPI) placed downstream of a mobility classifier. The aggregate length and primary particle size were obtained by analysis of the transmission electron microscope (TEM) images of more than 1000 diesel aggregates. The number of primary particles in an aggregate was related to the aggregate length and primary particle size by the Koylu et al. method (Koylu, U. 0., and Faeth, G. M., Farais, T. L., and Carvalho, M. G., "Fractal and Projected Structure Properties of Soot Aggregates", Comb. Flame. 100, 621 (1995)). The aggregate volume was then obtained by summing the volumes of all the primary particles that compose the aggregates. The primary particles were somewhat larger than the free molecular primary particles of idealized aggregates described above. The average primary particle diameter was 31.9±7.2 nm oriented parallel to flow with a normal distribution. The fractal dimension based on the projected length was 1.75. Accordingly, the aggregates were transparent, i.e., each primary particle was equally exposed to the gas molecules, similar to the idealized aggregates; therefore, the aggregate volume measurement can be used to verify Eq. 6.

Figure 8:
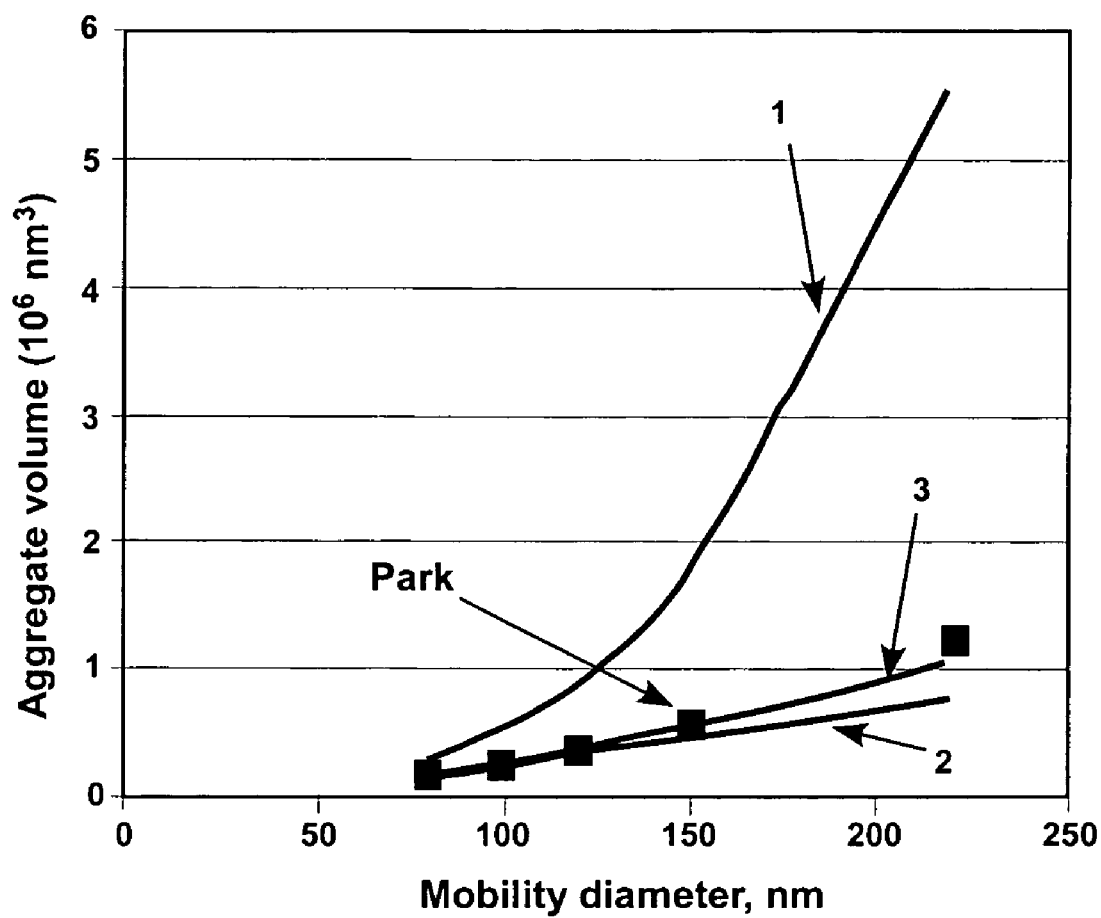
FIG. 8 is a graph comparing experimental data to theoretically calculated values.

FIG. 8 shows a comparison between idealized aggregate volumes obtained from Eq. 6 (curve 2), volume of spheres with the same mobility diameter (curve 1), and that obtained by Park et al. for diesel aggregates (square points). As shown in FIG. 8, the idealized aggregate volume calculated using the formulas set forth above (curve 2) is a much better estimate than that based on spheres. In these experiments, as the primary particles are somewhat larger than that of idealized aggregates, the adjusted sphere method according to Dahneke, B., was applied to obtain aggregate drag for Eq. 6. The corresponding aggregate volumes were then plotted in FIG. 8 as the middle curve (curve 3). Good agreement is found between the experimental aggregate volumes and that obtained from Eq. 6 (module 1).

By equating the migration velocities of aggregates and spheres that trace the same path in an electrical classifier, an expression was obtained for the number of primary particles in an aggregate with a given primary particle size in terms of its mobility diameter. The fact that the charge distribution on the aggregates is different from that of spheres with the same mobility diameter was taken into consideration. From the known charge distribution on the aggregates, the number, surface area and volume distributions for aggregates can be obtained as a function of mobility diameter.

This analysis permits a comparison between the surface area and volume distributions of aggregates with that of spheres of the same mobility diameter. Surface area distributions for randomly oriented aggregates are somewhat over predicted if the calculations are based on mobility diameter. For the same number and size of primary particles, the surface area based on mobility diameter is greater for aggregates with orientation perpendicular to the aggregate motion relative to the gas than those with parallel orientation. However, volume distributions are grossly over predicted if the calculations are based on the assumption of spherical particles with diameter equal to the mobility diameter.

The method described above for the online measurement of aggregate number, surface area and volume distributions was verified experimentally. The calculated number distribution for silver aggregates is in good agreement with the measured number distribution of spheres of sintered aggregates. The calculated aggregate volume is accurate to within about 5%. However, if the aggregate volume is calculated based on spheres with diameter equal to the mobility diameter the volume is overpredicted by a factor of about 2.4.

The method has been verified for idealized aggregates with low fractal dimension ($D_f<2$) and uniform free-molecular primary particle sizes. The test of the theoretical volumes using diesel aggregates with primary particle diameter of about 31.9±7.2 nm shows that the method gives a much better estimate than that based on spheres. The aggregate volumes calculated are in agreement with the experimental values irrespective of the spread in primary particle size (±7.2 nm).

Experimental results show that the aggregate number, surface area and volume distributions can be measured online using electric mobility analysis in conjunction with the formulas set forth above. In systems where the primary particle sizes do not vary significantly, this method can be immediately applied. Sources of error include the presence of aggregates with fractal dimension greater than 2, a distribution range in primary particle sizes and the formation of necks between the primary particles.

Improved modules for aggregate drag and charging can be used as more information becomes available. For example, Monte-Carlo simulations for bipolar diffusion charging similar to those of Biskos, G., Mastorakos, E., and Colings, N., "Monte-Carlo Simulation of Unipolar Diffusion Charging for Spherical and Nonspherical Particles", J. Aerosol Sci. 35, 707 (2004) for unipolar diffusion charging of aggregates should be more accurate than the prolate spheroid model used in our study. Calculation of drag on the aggregates is based on the assumption that the primary particles are in the free molecular regime. Extension to the transition regime may be much more difficult because the free molecule regime has a much simpler form for the drag dependence on primary particle size.

The foregoing Detailed Description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising the step(s) of . . . "

What is claimed is:

1. A method of estimating the number of nanoparticle aerosol aggregates having a primary particle size a in a gas using a differential mobility analyzer for measuring spherical particles, comprising:
   a) passing a volume of a gas containing entrained nanoparticle aerosol aggregates through the differential mobility analyzer for measuring spherical particles;
   b) obtaining the primary particle size a of the aggregates;
   c) obtaining a mobility diameter $d_m$ of the aggregates;
   d) counting a total number of aggregates $n_{sph}$ that pass through the differential mobility analyzer;
   e) equating a migration velocity of an aggregate to that of a spherical particle having the same mobility diameter $d_m$ to obtain a number N of primary particles in the aggregate particle;
   f) determining a fraction of aggregates $\eta_{agg}$ that are singly electrically charged by the differential mobility analyzer; and
   g) estimating the number of aggregates $n_{agg}$ in the volume of gas from the counted total number of aggregates $n_{sph}$ and the charge fraction $\eta_{agg}$.

2. The method of claim 1, wherein e) comprises using the expression $$\frac{d_m}{C(d_m)} = \frac{c^* N a^2}{3\pi\lambda}$$

where C is a slip correction coefficient, c* is a dimensionless drag force coefficient, and $\lambda$ is the mean free path of the gas.

3. The method of claim 2, wherein c* is approximately 9.17 for aggregates having random orientations.

4. The method of claim 2, wherein c* is approximately 6.62 for aggregates having orientations parallel to the flow of the gas.

5. The method of claim 2, wherein f) comprises using the expression $$\eta_{agg} = \frac{e}{(\pi D_{qe} kT)^{1/2}} \exp\left[\frac{-q^2 e^2}{D_{qe} kT}\right]$$

where q is the equivalent of one unit electric charge, e is the electric charge carried by a particle, $D_{qe}$ is a charging equivalent diameter of the aggregate as given by the expression $$D_{qe} = \frac{2aN}{\ln(2N)}.$$

6. The method of claim 5, wherein g) comprises using the expression $$n_{agg} = n_{sph} \frac{\eta_{sph}}{\eta_{agg}}$$

where $\eta_{sph}$ is the fraction of spherical particles that are singly electrically charged by the analyzer.

7. A method of estimating a surface area of nanoparticle aerosol aggregates in a gas having a primary particle size a using a differential mobility analyzer for measuring spherical particles, comprising:
   estimating the number of aggregates $n_{agg}$ in the gas by the method of claim 5; and
   estimating the surface area of the aggregates $A_{agg}$ using the expression $$A_{agg}(d_m) = \eta_{agg}(d_m) N(d_m) 4\pi a^2.$$

8. A method of estimating a volume of nanoparticle aerosol aggregates in a gas having a primary particle size a using a differential mobility analyzer for measuring spherical particles, comprising:
   estimating the number of aggregates $n_{agg}$ in the gas by the method of claim 5; and
   estimating the volume of the aggregates $V_{agg}$ using the expression $$V_{agg}(d_m) = \eta_{agg}(d_m) N(d_m) \left(\frac{4\pi a^3}{3}\right).$$

9. A method of estimating a surface area of nanoparticle aerosol aggregates in a gas having a primary particle size a using a differential mobility analyzer for measuring spherical particles, comprising:
   estimating the number of aggregates $n_{agg}$ in the gas by the method of claim 1; and
   estimating the surface area of the aggregates $A_{agg}$ using the expression $$A_{agg}(d_m) = \eta_{agg}(d_m) N(d_m) 4\pi a^2.$$

10. A method of estimating a volume of nanoparticle aerosol aggregates in a gas having a primary particle size a using a differential mobility analyzer for measuring spherical particles, comprising:
    estimating the number of aggregates $n_{agg}$ in the gas by the method of claim 1; and
    estimating the volume of the aggregates $V_{agg}$ using the expression $$V_{agg}(d_m) = \eta_{agg}(d_m) N(d_m) \left(\frac{4\pi a^3}{3}\right).$$

11. A computer-readable medium having computer-executable instructions thereon for causing a computer to estimate the number of nanoparticle aerosol aggregates having a primary particle size a in a volume of gas by:
    a) acquiring the primary particle size a of the aggregates in the volume of gas from the differential mobility analyzer for measuring spherical particles;
    b) acquiring a mobility diameter $d_m$ of the aggregates from the differential mobility analyzer;
    c) acquiring a total number of aggregates $n_{sph}$ that pass through the differential mobility analyzer;
    d) equating a migration velocity of an aggregate to that of a spherical particle having the same mobility diameter $d_m$ to obtain the number N of primary particles in the aggregate;
    e) determining a fraction of aggregates $\eta_{agg}$ that are singly electrically charged by the differential mobility analyzer; and f) estimating the number of aggregates $n_{agg}$ in the volume of gas from the counted total number of aggregates $n_{sph}$ and the charge fraction $\eta_{agg}$.

12. The computer-readable medium of claim 11, wherein e) comprises using the expression $$\frac{d_m}{C(d_m)} = \frac{c^* N a^2}{3\pi\lambda}$$

where C is a slip correction coefficient, $c^*$ is a dimensionless drag force coefficient, and $\lambda$ is the mean free path of the gas.

13. The computer-readable medium of claim 12, wherein $c^*$ is approximately 9.17 for aggregates having random orientations.

14. The computer-readable medium of claim 12, wherein $c^*$ is approximately 6.62 for aggregates having orientations parallel to the flow of the gas.

15. The computer-readable medium of claim 12, wherein f) comprises using the expression $$\eta_{agg} = \frac{e}{(\pi D_{qe} kT)^{1/2}} \exp\left[\frac{-q^2 e^2}{D_{qe} kT}\right]$$

where q is the equivalent of one unit electric charge, e is the electric charge carried by a particle, $D_{qe}$ is a charging equivalent diameter of the aggregate as given by the expression $$D_{qe} = \frac{2aN}{\ln(2N)}.$$

16. The computer-readable medium of claim 15, wherein g) comprises using the expression $$n_{agg} = n_{sph} \frac{\eta_{sph}}{\eta_{agg}}$$

where $\eta_{sph}$ is the fraction of spherical particles that are singly electrically charged by the analyzer.

17. A computer-readable medium having computer-executable instructions thereon for causing a computer to estimate a surface area of nanoparticle aerosol aggregates having a primary particle size a in a volume of gas by:
  estimating the number of aggregates $n_{agg}$ in the gas as set forth in claim 15; and
  estimating the surface area of the aggregates $A_{agg}$ using the expression $$A_{agg}(d_m) = \eta_{agg}(d_m) N(d_m) 4\pi a^2.$$

18. A computer-readable medium having computer-executable instructions thereon for causing a computer to estimate a volume of nanoparticle aerosol aggregates having a primary particle size a in a volume of gas by:
  estimating the number of aggregates $n_{agg}$ in the gas as set forth in claim 15; and
  estimating the volume of the aggregates $V_{agg}$ using the expression $$V_{agg}(d_m) = \eta_{agg}(d_m) N(d_m) \left(\frac{4\pi a^3}{3}\right).$$

19. A computer-readable medium having computer-executable instructions thereon for causing a computer to estimate a surface area of nanoparticle aerosol aggregates having a primary particle size a in a volume of gas by:
  estimating the number of aggregates $n_{agg}$ in the gas as set forth in claim 11; and
  estimating the surface area of the aggregates $A_{agg}$ using the expression $$A_{agg}(d_m) = \eta_{agg}(d_m) N(d_m) 4\pi a^2.$$

20. A computer-readable medium having computer-executable instructions thereon for causing a computer to estimate a volume of nanoparticle aerosol aggregates having a primary particle size a in a volume of gas by:
  estimating the number of aggregates $n_{agg}$ in the gas as set forth in claim 11; and
  estimating the volume of the aggregates $V_{agg}$ using the expression $$V_{agg}(d_m) = \eta_{agg}(d_m) N(d_m) \left(\frac{4\pi a^3}{3}\right).$$

* * * * *